United States Patent [19]
Klein

[11] Patent Number: 5,333,625
[45] Date of Patent: Aug. 2, 1994

[54] SUTURING WITH CORROSION AND BREAKAGE RESISTANT FLEXIBLE WIRE

[75] Inventor: Harvey A. Klein, Brooklyn, N.Y.
[73] Assignee: Rikki Brezak, Brooklyn, N.Y.
[21] Appl. No.: 803,707
[22] Filed: Dec. 4, 1991

Related U.S. Application Data

[63] Continuation of Ser. No. 488,726, Mar. 5, 1990, abandoned, which is a continuation-in-part of Ser. No. 233,534, Aug. 18, 1988, abandoned.

[51] Int. Cl.⁵ .............. A61B 19/00; A61B 17/60; C22F 1/00
[52] U.S. Cl. .............. 128/898; 606/222; 606/223; 606/228; 148/327; 148/336
[58] Field of Search .............. 606/222–228, 606/76, 103; 148/12 B, 12 E, 327; 128/898

[56] References Cited

U.S. PATENT DOCUMENTS 4,535,764  8/1985  Ebert .......................... 606/224
4,602,636  7/1986  Noiles ......................... 606/224

OTHER PUBLICATIONS

Maryland Specialty Wire, Inc. sale brochure for "BioWire" alloy wires fabricated from interalia, MP35N; an alloy which contains nickel, cobalt, chromium and molyddenum.
Annual Book of ASTM Standards; Sec 13 Medical Devices vol. 13.01., pp. 15–19, 32–35 and 214–217, 1916, Philadelphia, Pa.

*Primary Examiner*—Stephen C. Pellegrino
*Attorney, Agent, or Firm*—Israel Nissenbaum

[57] ABSTRACT

A suture or fixation wire having a relatively high degree of elasticity is utilized in suturing or fixation procedures in soft tissue or bone, with improvements in corrosion and breakage resistance and with reduction of tissue trauma. The wire is comprised of a medical grade low carbon content stainless steel, formed under low vacuum conditions in a substantially oxygen free environment and subsequently cold drawn into the wire configuration. The forming process provides the requisite flexibility and enhanced corrosion and breakage resistance without detrimentally affecting holding power. Alternatively, a cobalt-chromium or titanium wire is annealed or otherwise treated such as by modification of the chemical composition to reduce tensile strength by at least 10% for enhanced flexibility. The cobalt-chromium or titanium wire, though not as flexible as the low vacuum formed stainless steel, is preferably used in applications wherein a metal prosthesis has been implanted in the body. The same or similar metal composition of the suture or fixation wire is used in such applications in order to avoid the formation of an internal electrolytic cell with attendant corrosion.

1 Claim, 1 Drawing Sheet

SUTURING WITH CORROSION AND BREAKAGE RESISTANT FLEXIBLE WIRE

CROSS REFERENCE TO RELATED APPLICATION

This is a continuation of copending application Ser. No. 07/488,726 filed on Mar. 5, 1990, now abandoned which is a continuation-in-part of application Ser. No. 07/233,534 filed Aug. 18, 1988, now abandoned.

BACKGROUND OF THE INVENTION

1. Field of the Invention

This invention relates to materials utilized in surgical suturing and particularly surgical wire suturing.

2. Description of the Related Art

Surgical suture wire, as opposed to synthetic plastic or gut suture, is generally utilized in surgery wherein a high degree of holding power and infection resistance is required. Such applications include the repair of bone breaks, replacement of hips, sternum closures after cardiac surgery, closure of peritoneum in infected abdominal wounds (such as is common in battle field situations) and the like. It has accordingly been the practice in some of such applications to utilize high strength, corrosion resistant wire of gages 16–20 of titanium, cobalt-chromium or alloy stainless steel, etc., composition having a high tensile strength. For example, the 1983 ASTM standard F-642 (for Medical Devices) designates the maximum tensile strength for stainless steel wire for tissue fixation of between 210 and 200 ksi for a wire of between 0.01 (0.25 mm) to 0.05 (1.25 mm) inch diameter with an elongation of between 8–10%. Cobalt-chromium alloy flexible wire for bone fixation (ASTM F 644) in an 0.01 (0.25 mm) to 0.025 (0.63 mm) inch diameter has a tensile strength of about 185 to 165 ksi with an elongation of 35–40%. These wires, though considered to be flexible, are however, because of their very strength, relatively stiff compared to other suture materials such as of plastic. Accordingly, they are difficult to handle and cannot be readily manipulated to conform to bone surfaces or for exact placement in tissue fixation. Additionally, the stiffness of the wire may result in increased breakage of such wire during and after surgery. Incidence of breakage is further exacerbated with the use of wire tighteners such as disclosed in U.S. Pat. No. 4,527,554. Such wire tighteners prevent the application of marring stress on the wire by providing a movable surface against which the wire ends are biased during the tightening procedure. However, while they form nearly perfect helical ties without marring of the wire (and the formation of weak points), they concentrate stress at the base of the twisted connection. This concentrated stress can be detrimental to the shear, rather than tensile strength of the currently utilized relatively stiff suture wires. Another drawback encountered with the use of small diameter and the relatively stiff wires is that they have the cutting power of a cheese slicer with resultant tissue trauma, particularly if the wire connection is overtightened. Nevertheless, their use has been widespread because it has mistakenly been universally thought that these particular applications require high strength, stiffness and hardness.

In order to minimize tissue trauma and necrosis and infection resulting from overtightening and the "cheese cutter" effect, surgeons may tend to undertighten. Such compensation is however very detrimental, particularly with respect to approximation of the sternum following open heart surgery since undertightened sutures result in sternal "click", a detrimental condition caused by movement of one half of the sternum with respect to the other half, upon coughing or deep breathing. This causes the patient to avoid these maneuvers, thereby resulting in atalectasis and possibly pneumonia.

SUMMARY OF THE INVENTION

It is an object of the present invention to provide a method for improving suturing and fixation, and their after-effects, by the use of a specific stainless steel wire material as the wire suture.

It is a further object of the present invention to provide a more corrosion resistant stainless steel material for use in wire suturing which provides the advantages of decreased incidence of wire breakage, increased flexibility in handling and which nevertheless provides excellent holding strength.

It is another object of the present invention whereby the wire itself serves as the suturing needle or is used with pre-formed perforations.

It is a still further object of the present invention to provide a flexible cobalt-chromium alloy or titanium suturing or fixation wire, for use in applications wherein a metal prosthesis has been utilized and a similar metal is required to avoid the formation of a corrosive in vivo electrolytic cell.

These and other objects, features and advantages of the present invention will become more evident from the following discussion and drawings in which:

Figure 1:
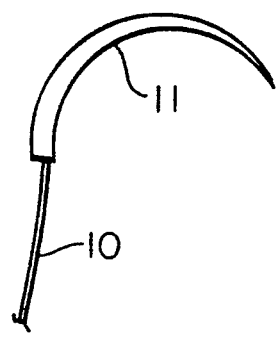
FIG. 1 is a surgical needle with swaged-in wire of the present invention.

Generally the present invention comprises a method for suturing with a stainless steel wire of special quality which unexpectedly provides surgical sutures of greater reliability and which wire is substantially easier to utilize. Ease of utilization is of particular importance during the rigors of a surgical procedure since the ease of utilization has a direct effect on the end result, the suture tie, which in turn affects the overall outcome and result of the entire surgical procedure, and ultimately, the patient's recovery. Stainless steel wire (ASTM F 642) currently being utilized for sutures, though its use is decreasing with the availability of the more preferred titanium and cobalt-chromium suture materials, is comprised of a low carbon (less than 0.03 wt. %) air melt material formed in a standard arc furnace and is air annealed to provide a bright condition and finish. It has been discovered that the same stainless steel composition (set forth in ASTM F 138 for surgical implants but specifically described as not applying to surgical fixation of soft tissue and bone) is in fact suitable for tissue and bone fixation, when initially formed, in a special substantially oxygen-free furnace, into stainless steel wire as a low vacuum melt material. The low vacuum melt process seems to provide a more uniform material, by eliminating process impurities, with resultant reduced number of weak points, thereby making it more breakage resistant and also stronger in its holding power. In addition, less possible sites for corrosion are introduced in the process. The low vacuum melt material of the present invention, because it is formed in a substantially oxygen free atmosphere, contains less impurities of materials such as oxides, silicates and sulfides and more corrosion resistance enhancing alloy materials such as molybdenum, chromium and nickel (12–14%).

The low vacuum melt formed stainless steel wire unexpectedly provides a suture material with suitable holding strength to hold proximate edges of separated soft tissue or bone in close contact during the entire regeneration process for enhanced healing. The low vacuum melt stainless steel wire of the present invention also has greater flexibility and greater breakage and corrosion resistance than the stainless steel wire used for surgical implants (ASTM F 138) and even that of stainless steel wire actually used for surgical fixation (ASTM F 642). In addition, the wire flexibility reduces the incidence of necrosis caused by the "cheese cutter" effect of the higher tensile strength wires of ASTM F 642. Furthermore, the low vacuum melt stainless steel wire of the present invention also has greater flexibility and corrosion resistance than titanium and cobalt-chromium materials. The low vacuum melt material of the present invention is prepared into suitable suture wire form by cold drawing through a die of suitable gage with the wire being further preferably annealed and polished. The resultant suture wire provides a tensile strength of about 130–105 ksi for wires of 0.01 (0.25 mm) to 0.04 (1.0 mm) inch diameters and an elongation of up to 45%. The wire is kept soft, flexible and malleable thereby giving it a good "hand" or feel. However, such tensile strength is considerably below that of the currently used suture wires. Yet surprisingly, such enhanced flexibility and breakage and corrosion resistance is without significant loss of holding strength.

DESCRIPTION OF THE PREFERRED EMBODIMENT

In accordance with the present invention, the aforementioned stainless steel wire is used in a method for improving suturing of soft tissue and bone with surgical wire, comprising the steps of:

a) suturing separated soft tissue or bone together with wire consisting essentially of stainless steel having a maximum carbon content of about 0.03%, i.e. the F 138 ASTM standard for material composition. As described, the stainless steel wire is formed in a substantially oxygen free furnace under conditions of low vacuum melting, then cold drawn into an elongated wire of the desired gage and then annealed. The resulting wire provides a uniform tensile strength of about 130–105 ksi for wires of 0.010 to 0.05 (0.25 to 1.25 mm) inch diameters. The suturing step is accomplished in one of three ways, the wire is swaged into the end of a standard surgical needle, the wire is cut diagonally to form its own point (because of the vacuum melting process, the wire has sufficient strength to act as its own needle), or, particularly with respect to bone fixation, the wire is blunted for insertion into pre-formed perforations;

b) tightening the wire whereby adjacent separated portions of the soft tissue or bone are brought into close proximate contact to facilitate healing; and c) twisting the ends of the wire into a tie whereby the sutured portion of the soft tissue or bone kept in close proximate contact during healing.

The low vacuum melt material provides a lower yield and lower tensile strength in the cold worked and/or annealed state and is more malleable and less brittle than the currently used stainless steel wire suture and therefore provides a greater fatigue loading which is of particular importance in suturing applications. Furthermore, because it is more malleable, it is better able to conform to bones and the like in providing stronger and more reliable connections but without the necrosis and/or strangulation commonly occurring with standard stainless steel sutures. The flexible low vacuum melt wire is also ideal for utilization with the wire tightening tool disclosed in U.S. Pat. No. 4,527,554 which provides nearly perfect helical wire tightening and reduced stress points. The flexibility of the low vacuum melt wire negates any possible ill effects of stress concentration at the base of a helical connection. The slow hardening, annealing and better surface finish of the low vacuum melt wire of the present invention also results in a lower friction in passing through tissues with concomitant lessening of tissue micro-trauma, and therefore, enhanced healing. Furthermore, there are very few, if any impurity inclusions in the metal surface, which in prior art suture materials, causes weak stress points which often result in early failure under fatigue loading.

In certain applications, wherein a patient has been provided with a metal prosthesis of a metal other than stainless steel, such as of cobalt-chromium alloy or titanium, it is preferred that a suture or fixation wire be utilized with the same or similar composition to avoid the formation of an in vivo electrolytic cell. In accordance with the present invention, after formation of the wire of the appropriate composition, it is annealed to an extent whereby its tensile strength is reduced by at least 10% to enhance its flexibility. Other means of reduction of tensile strength include changes in chemical composition and the like. Though not as flexible as low vacuum melt stainless steel, there is nevertheless a substantial enhancement in ease of handling, reduction of breakage and substantial negation of the "cheese cutter" effect.

Figure 2:
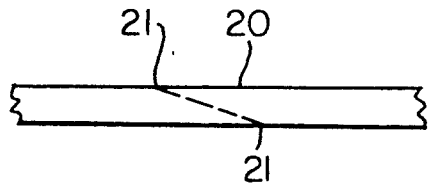
FIG. 2 depicts a portion of wire of the present invention with a sharp point formed by a diagonal cut.
Figure 3:
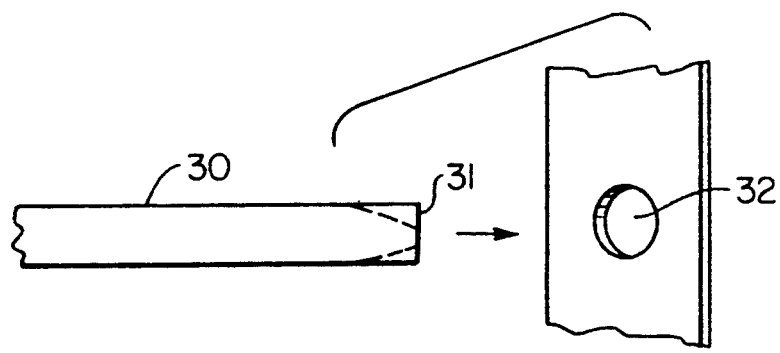
FIG. 3 depicts a portion of wire of the present invention with a blunted end for insertion into preformed perforations.

With reference to the drawings, FIG. 1 depicts wire 10 swaged into the rear of a surgical needle 11. FIG. 2 depicts wire 20 diagonally cut (shown by dashed lines) to form point 21 for use whereby the wire 20 can be used as its own needle in soft tissue. FIG. 3 depicts wire 30 with an end 31 blunted (shown by dashed lines) to facilitate insertion into preformed perforations 2 such as in bones.

It is understood that above description is illustrative of the present invention and that changes in wire dimension, configuration, composition and suturing utilization are possible without departing from the scope of the present invention as defined in the following claims.

What claim is:

1. A method for improving suturing of soft tissue and bone with surgical wire, comprising the steps of: a) suturing separated soft tissue or bone together with wire consisting essentially of stainless steel, comprising from 17 to 19% chromium, 12 to 14% nickel and at least about 61% iron and having a maximum carbon content of about 0.03%, said stainless steel wire having been formed in a substantially oxygen free furnace under conditions of low vacuum melting, then cold drawn into an elongated wire of the desired gage and then annealed; whereby said wire provides a uniform tensile strength of about 130–105 ksi for wires of 0.010 to 0.05 (0.25 to 1.25 mm) inch diameters; b) tightening the wire whereby adjacent separated portions of the soft tissue or bone are brought into close proximate contact to facilitate healing; and c) twisting the ends of the wire into a tie whereby the sutured portions of the soft tissue or bone are kept in said close proximate contact during healing.

* * * * *